(12) United States Patent
Nakayama et al.

(10) Patent No.: US 6,531,165 B2
(45) Date of Patent: *Mar. 11, 2003

(54) COLLAGEN PRODUCTION PROMOTER COMPOSITION

(75) Inventors: Yasukazu Nakayama, Yokohama (JP); Nao Kojima, Tokyo (JP)

(73) Assignee: Shiseido Company, Ltd., Tokyo (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/472,438

(22) Filed: Dec. 27, 1999

(65) Prior Publication Data

US 2002/0168425 A1 Nov. 14, 2002

Related U.S. Application Data

(62) Division of application No. 09/155,012, filed on Sep. 16, 1998.

(30) Foreign Application Priority Data

Jan. 17, 1997 (JP) .............................................. 9-19673

(51) Int. Cl.$^7$ .............................................. A61K 35/78
(52) U.S. Cl. ....................... 424/769; 424/725; 424/779; 514/844
(58) Field of Search ............................. 424/195.1, 725, 424/769, 779; 514/844

(56) References Cited

U.S. PATENT DOCUMENTS

| 5,035,887 A | 7/1991 | Antoniades et al. ....... 424/85.2 |
| 6,080,393 A | * 1/2000 | Liu et al. |

FOREIGN PATENT DOCUMENTS

| CH | 686 999 | 8/1996 |
| FR | 2 753 374 | 3/1998 |
| WO | 97/31620 | 9/1997 |

OTHER PUBLICATIONS

Matsumoto, K. Fragr. J. 1996. vol. 24 (8), pp. 81–84, JICST–EPlus Abstract enclosed.*
J. Lawless, in The Illustrated Encyclopedia of Essential Oils, The Complete Guide to the Use of Oils in Aromatherapy and Herbalism, Element Books, Inc., MA, p. 48, 1996.*
C. Hobbs, in "Hanbook For Herbal Healing, A Concise Guide To Herbal Products", Botanica Press, Capitola, CA, pp. 16 and 23, 1995.*
Frawley et al., in "The Yoga of Herbs, An Ayurvedic Guide to Herbal Medicine", Lotus Press, WI, pp. 78–79, 1992.*
Fevrier; "Fagus Silvatica Extract"; Nature Extracts; vol. 119, No. 3; Feb. 1993; pp. 142–147; XP–000343313.
Pourrat et al.; "A Beech bud Extract"; Cosmetic & Toiletries; vol. 110, No. 8; Aug. 1995; pp. 59–63; XP–000879477.
Database WPI; Week 9934; XP–002130741; JP 11–158054; Abstract.
Koichi; "Preparation for External Use for Skin"; Patent Abstracts of Japan; vol. 1998;, No. 01; Jan. 30, 1998; JP 09–227397; Sep. 2, 1997; Abstract.

* cited by examiner

*Primary Examiner*—Christopher R. Tate
(74) *Attorney, Agent, or Firm*—Foley & Lardner

(57) ABSTRACT

A collagen production promoter composition according to the present invention containing an extract from a shoot of a tree belonging to the Fagaceae Fagus, particularly a young shoot, as an active component, which exhibits a superior effect of prevention of aging by promoting the production of collagen, which is one of the components of the extracellular matrix, and the activation of the excellular matrix and normalization of the skin tissue based on the promotion of production of collagen.

2 Claims, 1 Drawing Sheet

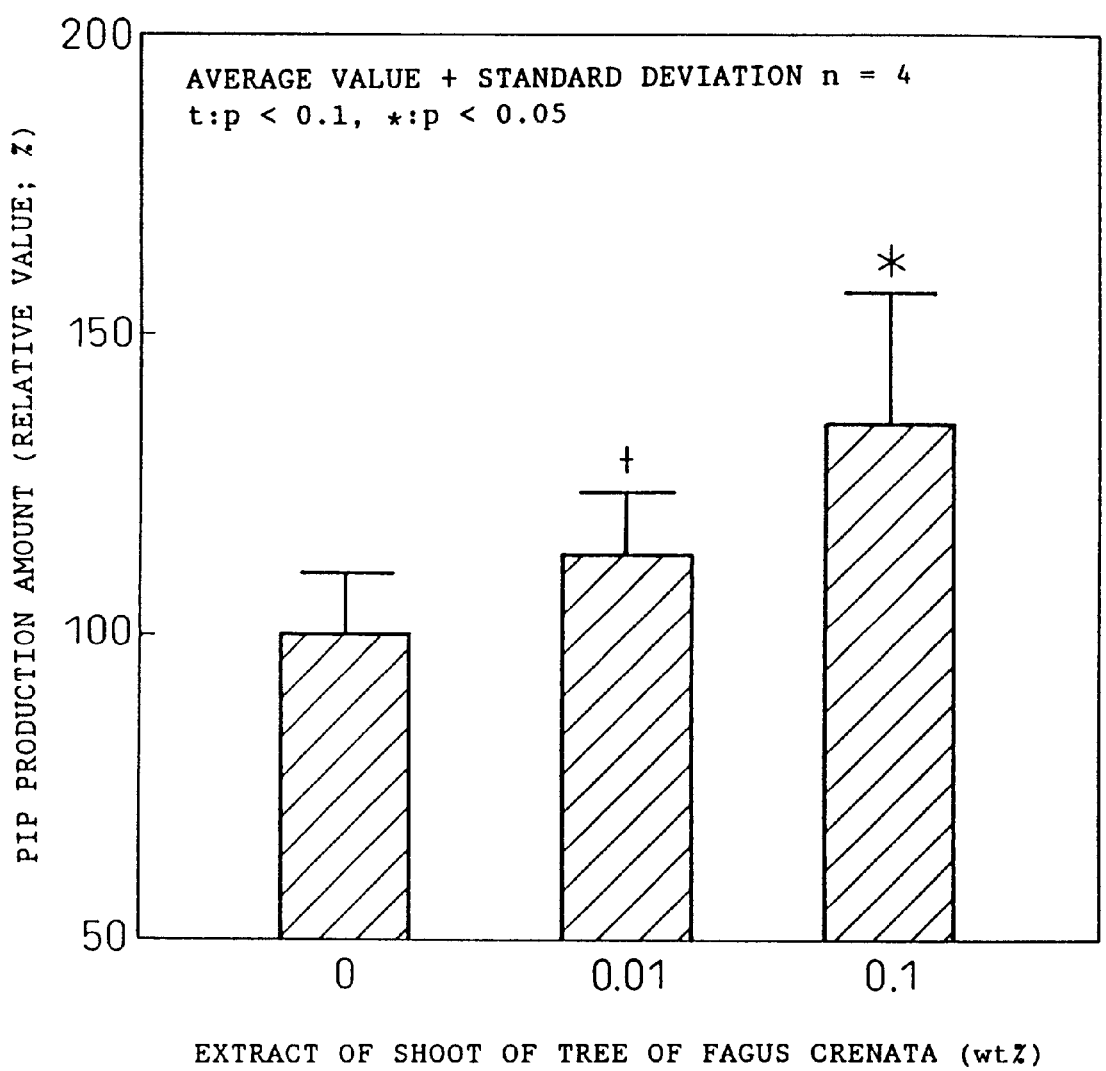

COLLAGEN PRODUCTION PROMOTER COMPOSITION

This application is a divisional of application Ser. No. 09/155,012, filed Sep. 16, 1998.

TECHNICAL FIELD

The present invention relates to a collagen production promoter composition for promoting the production of collagen, which is one of the components of the extracellular matrix.

BACKGROUND ART

The shoots of plants are the stage before budding. In preparation for the budding, large amounts of active ingredients such as plant hormones are stored in the shoots. Medical treatments using these highly active ingredients have been known in Europe since the 1960s as "Gemmotherapy".

On the other hand, subject, aging proceeds in all organs of the body. However, looking at aging of the skin, which can be visually discerned, especially the face, which people easily focus their attention on, changes in appearance such as wrinkles and crow's feet, stains and age spots, sagging, loss of tautness and gloss trouble many of the middle aged and elderly in the world, particularly women. Up until now, the need for an anti-aging cosmetic has been pointed to, but since there was much about the mechanism, definition, etc. of aging that had not been clear, in conventional cosmetics, the method had been adopted of trying to maintain moisture by adding biochemical product or synthetic polymer product such as a mucopolysaccharide, collagen. However, it became clearer that, with this alone, it was not possible to sufficiently prevent aging of the skin.

However, in recent years, there have been studies advanced on aging. As the causes for aging of the skin, viewed macroscopically, actual years has been an important factor. Further, drying, oxidation, the effects of sunlight (UV rays), etc. have been mentioned as direct factors relating to skin aging. Further, it has become clear that, at the skin of the face, there is a remarkable decline in the collagen fiber, which is the most important component of the matrix of the dermis. Further, it is suggested that the occurrence of wrinkles and crow's feet and the loss of tautness are closely related to the decline in the collagen fiber.

In this way, when it comes to aging of the skin, various skin aging factors cause a decline in the proliferation of fibroblasts, important cells in the dermis, and the capability to biosynthesize collagen and the like, typical components of the extracellular matrix in the skin, and consequently cause a slowdown in the speed of turnover of the collagen etc. As a result, the elasticity of the skin is lost, wrinkles and sagging increase, and aging of the skin progresses.

Under the above-mentioned circumstances, there has been a demand for a collagen production promoter which promotes the biosynthesis of collagen, which is one of the important components in the dermis, so as to prevent aging of the skin and which is free from problems in safety.

DISCLOSURE OF INVENTION

Accordingly, the object of the present invention is to provide a collagen production promoter composition having an action promoting biosynthesis of collagen, which is one of the important components of the extracellular matrix of the skin, by acting on the fibroblasts in the skin.

In accordance with the present invention, there is provided a collagen production promoter composition comprising an extract from a shoot of a tree belonging to Fagaceae Fagus, as an active component, in a base component.

BRIEF DESCRIPTION OF THE DRAWINGS

The present invention will now be further explained with reference to the drawing.

FIG. 1 is a view showing the relationship between an extract of a shoot of a tree belonging to the *Fagus crenata* obtained in Test Example 1 and the amount of production of PIP.

BEST MODE FOR CARRYING OUT THE INVENTION

The present invention now will now be explained in further detail.

The extract from a shoot of a tree belonging to the Fagaceae Fagus which can be used in the present invention is obtained from a shoot of the *Fagus crenata* Blume, *Fagus japonika* Maxim, *Fagus grandifolia*, *Fagus sylvatica* L., *Fagus sylvatica* L. var. *pendula, Fagus sylvatica* L. var. *purpurea, Fagus orientalis* Lipsky, etc. alone or in mixtures of two or more types. For the extraction, solvents usually used at the time of production of a cosmetic material such as water, ethanol, methanol, propanol, butanol, 1,3-butylene glycol are used alone or in any mixtures thereof. The shoot of a tree belonging to the Fagus used in the present invention is observed to be effective if it is the shoot part, but the use of a young shoot is preferable because of higher effectiveness.

Note that there have not been any reports regarding the action of promotion of the production of collagen of an extract from a shoot of a tree belonging to the Fagaceae Fagus up to now.

As an extract from a shoot of the tree belonging to the Fagus of the present invention, for example, GATULINE (registered trademark) RC and GATULINE (registered trademark) R manufactured and marketed by Gattfossé S. A. of France may be mentioned.

For the collagen production promoter composition according to the present invention, one or more types of extracts from shoots, preferably young shoots, of these trees belonging to the Fagus can be optionally selected.

The amount blended is preferably 0.0001 to 30.0% by weight, more preferably 0.001 to 10.0% by weight, based upon the total amount of the collagen production promoter composition.

The collagen production promoter composition of the present invention promotes the production of collagen, which is one of the components of the extracellular matrix, and achieves the desired object purpose for exhibiting the superior effect of preventing aging by activating the extracellular matrix and restoring the skin tissue to normal based on the promotion of the production of collagen.

Other medicinal ingredients may be formulated into the collagen production promoter composition of the present invention so long as they do not detract from the desired effect.

For example, to impart a moisturizing effect etc., moisturizers such as polyethylene glycol, propylene glycol, glycerin, 1,3-butylene glycol, hexylene glycol, xylitol, sorbitol, maltitol, chondroitin sulfuric acid, hyaluronic acid, mucoitin sulfuric acid, caronic acid, atelocollagenous protein, cholesteryl-12-hydroxystearate, sodium lactate, gallates, dl-pyrrolidone carboxylates, short chain soluble collagenous protein, diglycerin (EO) PO adducts, Hestnut rose (*Rosa roxburghii*) extract, Yarrow (*Achillea millefolium*) extract, Sweet clover (*Melilotus officinalis*) extract, tranexamic acid may be formulated into the collagen production promoter composition of the present invention.

Giving a whitening effect is useful for the purpose of relieving the harmful effects of UV rays, which is one of the major factors behind skin aging, on the skin. In this case, whiteners such as placenta extract, glutathione, saxifrage extract, albutin may be formulated into the collagen production promoter composition of the present invention.

Giving an antiphlogistic effect is useful for the purpose of relieving the harmful effects of UV rays on the skin in the same way as above. In this case, antiphlogistic agents such as a glycyrrhizic acid derivative, glycyrrhetic acid derivative, salicylic acid derivative, hinokitiol, zinc oxide, allantoin may be formulated into the collagen production promoter composition of the present invention.

Similarly, for the purpose of relieving the harmful effects of UV rays on the skin etc., activating agents such as royal jelly, photosensitive agents, cholesterol derivatives, fetal calf serum extract; blood circulation promoters such as nonylate valenyl amide, nicotinate benzyl esters, nicotinate β-butoxyethyl esters, capsaicine, zingerone, cantharis tincture, ichthammol, caffeine, tannic acid, α-borneol, tocopherol nicotinate, inositol hexanicotinate, cyclandelate, cinnarizine, trazoline, acetylcholine, verapaml, cepharanthine, γ-orzanol; antiseborrheics such as sulfur, thianthol, etc. may be formulated into the collagen production promoter composition of the present invention.

Further, for the purpose of easing the adverse effect of UV rays on the skin, a UV protective agent may be formulated into the collagen production promoter composition of the present invention.

That is, as the P long wavelength UV ray (UVA) absorbers, anthranilate base UV absorbers such as methyl anthranilate, homomentyl-N-acetylanthranilate; benzophenone base UV absorbers such as 2,4-dihydroxybenzophenone, 2,2-dihydroxy-4-methoxybenzophenone, 2,2'-dihydroxy-4,4'-dimethoxybenzophenone, 2,2',4,4'-tetrahydroxybenzophenone 2-hydroxy-4-methoxybenzophenone, 2-hydroxy -4-methoxy-4'-methylbenzophenone, 2-hydroxy-4-methoxybenzophenone-5-sulfonic acid, 4-phenylbenzophenone, 2-ethylhexyl-4'-phenyl-benzophenone-2-carboxylate, 2-hydroxy-4-n-octoxybenzophenone, 4-hydroxy-3-carboxybenzophenone; benzotriazole base UV absorbers such as 2,2'-hydroxy-5-methylphenylbenzotriazole, 2-(2'-hydroxy-5'-t-octylphenyl)benzotriazole, 2-(2'-hydroxy-5'-methylphenyl)benzotriazole; dianisoylmethane, 4-methoxy -4'-t-butyldibenzoylmethane, etc. may be mentioned.

Among these UVA absorbers, 4-methoxy-4'-tert-butyldibenzoylmethane, 2-hydroxy-4-methoxybenzophenone, and 2-hydroxy-4-methoxybenzophenone derivatives, for example, 2-hydroxy-4-methoxy-benzophenone-5-sulfonates are those superior in safety and effectiveness.

Further, as P medium wavelength UV ray (UVB) absorbers, benzoate base UV absorbers such as paraaminobenzoic acid (hereinafter referred to as "PABA"), PABA monoglycerin ester, N,N-dipropoxy-PABA-ethyl ester, N,N-diethoxy-PABA ethyl ester, N,N-dimethyl-PABA-ethyl ester, N,N-dimethyl-PABA-butyl ester, N,N-dimethyl-PABA-amyl ester; salicylate base UV absorbers such as dipropylene glycol salicylate, ethylene glycol salicylate, myristyl salicylate, methyl salicylate, amyl salicylate, menthyl salicylate, homomenthyl salicylate, octyl salicylate, phenyl salicylate, benzyl salicylate, p-isopropanolphenyl salicylate; cinnamate base UV absorbers such as octyl cinnamate, ethyl-4-isopropyl cinnamate, methyl-2,5-diisopropyl cinnamate, ethyl-2,4-diisopropyl cinnamate, methyl-2,4-diisopropyl cinnamate, propyl-p-methoxy cinnamate, isopropyl-p-methoxy cinnamate, isoamyl-p-methoxy cinnamate, octyl-p-methoxy cinnamate (2-ethylhexyl-p-methoxy cinnamate), 2-ethoxyethyl-p-methoxy cinnamate, cyclohexyl-p-methoxy cinnamate, ethyl-α-cyano-β-phenyl cinnamate, 2-ethylhexyl-α-cyano-β-phenyl cinnamate, glycerylmono-2-ethylhexanoyl-diparamethoxy cinnamate (or mono-2-ethylyhexanoic glyceryl diparamethoxy cinnamate), octyl methoxycinnamate, 3,4,5-trimethoxycinnamate-3-methyl-4-[methylbis(trimethylsiloxy)silyl]butyl, p-dimethoxycinnamate mono-ethyl esters; camphor derivatives such as 3-(4'-methylbenzylidene)-d,1-camphor, 3-benzylidene-d,1-camphor, 5-(3,3-dimethyl-2-norbornylidene)-3-penten-2-one; urocanic acid, urocanate ethyl esters, 2-phenyl-5-methylbenzoxazole, dibenzalazine, etc. may be mentioned.

Further, as the UV scattering agents, titanium oxide ($TiO_2$) talc ($MgSiO_2$), carmine ($FeO_2$), bentonite, kaolin, zinc oxide (ZnO), etc. may be mentioned.

Further, for various purposes, plant extracts such as phellodendron bark extract, *Japanese coptis* extract, lithospermum root extract, peony root extract, swertia herb extract, birch extract, sage extract, loquat leaf extract, ginseng extract, aloe extract, mallow extract, iris extract, grape extract, coix extract, sponge gourd extract, lily extract, saffran extract, cnidium rhizome extract, ginger extract, hypericum extract, restharrow extract, rosemary extract, garlic extract, cayenne extract, citrus unshiu peel extract, *Japanese angelica* root extract may be formulated into the collagen production promoter composition of the present invention.

Further, to further give the inherent effects of various vitamins to the collagen production promoter composition of the present invention, vitamin A's such as vitamin A oil, retinol, retinol acetate; vitamin $B_2$'s such as riboflavin, riboflavin butyrate, flavinadenine nucleotide; vitamin $B_6$'s such as pyridoxine hydrochlorates, pyridoxine dioctanoates; vitamin C's such as L-ascorbic acid, L-ascorbate dipalmitate esters, L -ascorbate monopalmitate esters, sodium L-ascorbate-2-sulfate, L-ascorbate phosphate esters, L-ascorbate stearate esters, L-ascorbate-2-glycoside, dipotassium DL-α-tocopherol-L-ascorbate phosphate diester; pantothenic acids such as calcium pantothenate, D-pantothenyl alcohol, pantothenyl ethyl ether, acetyl pantothenyl ethyl ether; vitamin D's such as ergocalciferol, cholecalciferol; nicotinic acids such as nicotinic acid, nicotinic acid amide, benzyl nicotinate; vitamin E's such as α-tocopherol, tocopherol acetate, DL-α-tocopherol nicotinate, DL-α-tocopherol succinate; vitamin P, biotin, and other vitamins may be formulated into the collagen production promoter composition of the present invention.

Among these vitamins, when vitamin C's such as L-ascorbic acid, L-ascorbate dipalmitate esters, L -ascorbate monopalmitate esters, sodium L-ascorbate-2-sulfate, L-ascorbate phosphate esters, L-ascorbate stearate esters, L-ascorbate-2-glycoside, dipotassium DL -α-tocopherol-L-ascorbate phosphate diester are incorporated into the collagen production promoter composition of the present invention, a synergistic effect of promotion of the production of collagen is observed.

Note that the other medicinal ingredients which may be formulated into the collagen production promoter composition of the present invention are not limited to the above-mentioned medicinal ingredients. Further, the corresponding medicinal effects of the other medicinal ingredients mentioned above are not limited to the above. For example, vitamin C's may be used as whitening components and may also be used as anti-oxidation adjuvants. Further, the medicinal components mentioned above may be formulated into the collagen production promoter composition of the present invention alone or two or more of the above medicinal components may be optionally formulated in suitable combinations according to the purpose.

The present invention can be applied to a wide range of cosmetics, quasidrugs, etc. used for the external skin. It may take a broad range of forms such as aqueous solutions, dissolvable systems, emulsions, powders, oils, gels, ointments, aerosols, water-oil two-phase systems, water-oil-powder three-phase systems, etc. That is, in the case of basic cosmetics, it may be applied in the above various forms for facial cleansers, toilet water, emulsions, creams, gels, essences (beauty lotions), packs, masks, and other types of cosmetics. Further, if a makeup cosmetic, it may be used for a wide range of types of cosmetics such as foundations while in the case of a toiletry product it may be used for body soap, facial soap, etc. Further, in the case of a quasidrug, it can be used for a wide range of applications such as various ointments. Further, the types of the collagen production promoter composition of the present invention are not limited to these forms and types.

Further, the collagen production promoter composition of the present invention acts on the area around the hair roots and the scalp and is effective in protecting the scalp, and therefore, can be used also as, for example, a shampoo, rinse, treatment, conditioner, or other hair product.

In the collagen production promoter composition of the present invention, it is possible to formulate in a broad range of the usual known base components depending upon the above desired form and type to an extent where this formulation does not impair the desired effect of the present invention.

That is, as a liquid oil, avocado oil, tsubaki oil, primrose oil, turtle oil, macadamia nut oil, corn oil, mink oil, olive oil, rapeseed oil, egg oil, sesame oil, persic oil, wheat germ oil, sasanqua oil, castor oil, linseed oil, safflower oil, cottonseed oil, perilla oil, soybean oil, peanut oil, teaseed oil, kaya oil, rice bran oil, China wood oil, Japanese wood oil, jojoba oil, germ oil, triglycerin, glycerin trioctanate, glycerin triisopalmitate, etc., as the solid oils and fats, cacao butter, coconut oil, horse fat, hydrogenated coconut oil, palm oil, beef tallow, sheep fat, hydrogenated tallow, palm kernal oil, hog fat, beef bone fat, Japan wax nut oil, hydrogenated oil, beef hoof fat, Japan wax, hydrogenated castor oil, etc., as the waxes, beeswax, candelilla wax, cotton wax, carnauba wax, bayberry wax, insect wax, spermaceti, montan wax, rice bran wax, lanolin, kapok wax, lanolin acetate, liquid lanolin, sugarcane wax, isopropyl lanolin fatty acid, hexyl laurate, hydrogenated lanolin, jojoba wax, hard lanolin, shellac wax, POE lanolin alcohol ether, POE lanolin alcohol acetate, POE cholesterol ether, polyethylene glycol lanolin fatty acid, POE hydrated lanolin alcohol ether, etc., and as the hydrocarbon oils, liquid paraffin, ozokerite, squalane, pristane, paraffin, ceresine, squalene, vaseline, microcrystalline wax, and other oils may be mentioned.

As a higher fatty acid, for example, lauric acid, myristic acid, palmitic acid, stearic acid, behenic acid, oleic acid, 12-hydroxystearic acid, undecylic acid, toluic acid, isostearic acid, linolic acid, linoleic acid, eicosapentaenoic acid (EPA), docosahexaenoic acid (DHA), etc. may be mentioned.

As a higher alcohol, for example, linear alcohols such as lauryl alcohol, cetyl alcohol, stearyl alcohol, behenyl alcohol, myristyl alcohol, oleyl alcohol, cetostearyl alcohol; and branched alcohols such as monostearyl glycerin ether (batyl alcohol), 2-decyltetradecinol, lanolin alcohol, cholesterol, phytosterol, hexyldodecanol, isostearyl alcohol, octyldecanol, etc. may be mentioned.

As synthetic ester oils, isopropyl myristate, cetyl octanate, octyldodecyl myristate, isopropyl palmitate, butyl stearate, hexyl laurate, myristyl myristate, decyl oleate, hexyldecyl dimethyloctanate, cetyl lactate, myristyl lactate, lanolin acetate, isocetyl stearate, isocetyl isostearate, cholesteryl 12-hydroxystearate, ethylene glycol di-2-ethylhexylate, dipentaerythritol fatty acid ester, N-alkylglycol monoisostearate, neopentylglycol dicaproate, diisostearyl malate, glycerin di-2-heptyl undecanoate, trimethylopropane tri-2-ethylhexylate, trimethylopropane triisostearate, pentanerythritol tetra-2-ethylhexylate, glycerin tri-2-ethylhexylate, trimethylopropane triisostearate, cetyl-2-ethylhexanoate, 2-ethylhexyl palmitate, glycerin trimyristate, glyceride tri-2-heptylundecanoate, castor oil fatty acid methyl ester, oil oleate, cetostearyl alcohol, acetoglyceride, 2-heptylundecyl palmitate, diisobutyl adipate, N-lauroyl-L-glutamate-2-octyl dodecyl ester, di-2-heptylundecyl adipate, ethyl laurate, di-2-ethylhexyl sebatate, 2-hexyldecyl myristate, 2-hexyldecyl palmitate, 2-hexyldecyl adipate, diisopropyl sebatate, 2-ethylhexyl succinate, ethyl acetate, butyl acetate, amyl acetate, triethyl citrate, etc. may be mentioned.

As silicones, linear polysiloxanes such as dimethyl polysiloxane, methylphenyl polysiloxane, methylhydrogen polysiloxane, cyclic polysiloxanes such as decamethyl polysiloxane, dodecamethyl polysiloxane, tetramethyltetrahydrogen polysiloxane, silicone resins forming 3 dimensional net structures, silicone rubber, etc. may be mentioned.

As anionic surfactants, for example, fatty acid soaps such as soap ingredients, sodium laurate, sodium palmitate; higher alkyl sulfate ester salts such as sodium laurosulfate, potassium laurosulfate; alkyl ether sulfate ester salts such as POE laurosulfate triethanol amine, sodium POE laurosulfate; N-acylsarcosine acids such as sodium lauroyl sarcosinate; higher fatty acid amide sulfonates such as sodium N-myristoyl-N-methyl taurine, sodium N-cocoyl-N-methyl taurid, sodium laurylmethyl taurid; phosphate ester salts such as sodium POE oleyl ether phosphate, POE stearyl ether phosphate; sulfosuccinates such as sodium di-2-ethylhexylsulfosuccinate, sodium monolauroylmonoethanol amide polyoxyethylene sulfosuccinate, sodium laurylpolypropylene glycol sulfosuccinate; alkylbenzensulfonates such as linear sodium dedecylbenzensulfonate, linear dodecylbenzensulfonate triethanol amine, linear dodecyl benzensulfate; N-acyl glutamates such as monosodium N-lauroyl glutamate, disodium N-stearoyl glutamate, monosodium N-myristoyl-L -glutamate; higher fatty acid ester sulfate ester salts such as sodium hydrogenated glyceryl cocoate sulfate; sulfated oils such as Turkey red oil; POE alkyl ether carboxylic acid, POE alkylaryl ether carboxylate, α-olefinsulfates, higher fatty acid ester sulfonates, secondary alcohol sulfate ester salts, higher fatty acid alkylolamide sulfate ester salts, sodium lauroyl monoethanolamide succinate, N-palmitoyl asparaginate ditriethanol amine, sodium caseine, etc. may be mentioned.

As cationic surfactants, for example, alkyl trimethyl ammonium salts such as stearyl trimethyl ammonium chloride, lauryl trimethyl ammonium chloride; alkyl pyridinium salts such as distearyldimethyl ammonium chloride, dialkyldimethyl ammonium chloride salts, poly(N,N'-dimethyl-3,5-methylenepiperidinium)chloride, cetylpyridinium chloride; alkyl quaternary ammonium salts, alkyl dimethylbenzyl ammonium salts, alkyl isoquinolinium salts, dialkyl morphonium salts, POE alkyl amines, alkyl amine salts, polyamine fatty acid derivatives, amyl alcohol fatty acid derivatives, benzalkonium chloride, benzethonium chloride, etc. may be mentioned.

As amphoteric surfactants, for example, imidazoline base amphoteric surfactants such as sodium 2-undecyl -N,N,N-(hydroxyethylcarboxymethyl)-2-imidazoline, 2-cocoyl-2-imidazoliniumhydroxide-1-carboxyethyloxy-2-sodium salt; betaine base surfactants such as 2-heptadecyl-N-carboxymethyl-N-hydroxyethylimidazolinium betaine, lauryldimethyl-aminoacetate betaine, alkyl betaine, amide betaine, sulfo betaine; etc. may be mentioned.

As lyophilic nonionic surfactants, for example, sorbitan fatty acid esters such as sorbitan monooleate, sorbitan monoisostearate, sorbitan monolaurate, sorbitan monopalmitate, sorbitan monostearate, sorbitan sesquioleate, sorbitan trioleate, diglyceryl sorbitan penta-2-ethylhexylate, diglyceryl sorbitan tetra-2-ethylhexylate; glyceryl polyglyceryl fatty acids such as glyceryl monocottonseed fatty acid, glyceryl monoerucate, glyceryl sesquioleate, glyceryl monostearate, glyceryl α,α-oleate pyroglutamate, glyceryl monostearate malate; propylene glycol fatty acid esters such as propylene glycol monostearate; hydrogenated castor oil derivatives, glyceryl alkyl ethers, polyoxyethylene methylpolysiloxane copolymers, etc. may be mentioned.

As hydrophilic nonionic surfactants, for example, POE sorbitan fatty acid esters such as POE sorbitan monooleate, POE-sorbitan monostearate, POE-sorbitan monoolate, POE-sorbitan tetraoleate; POE sorbite fatty acid esters such as POE-sorbite monolaurate, POE-sorbite monooleate, POE-sorbite pentaoleate, POE-sorbite monostearate; POE glyceryl fatty acid esters such as POE-glyceryl monostearate, POE-glyceryl monoisostearate, POE-glyceryl triisostearate; POE fatty acid esters such as POE monooleate, POE distearate, POE monodioleate, distearate ethylene glycol; POE alkyl ethers such as POE lauryl ethers, POE oleyl ethers, POE stearyl ethers, POE behenyl ethers, POE2-octyldodecyl ethers, POE cholestanol ethers; POE alkyl phenyl ethers such as POE octyl phenyl ethers, POE nonyl phenyl ethers, POE dinonyl phenyl ethers; pluaronics such as Pluronic; POE-POP alkyl ethers such as POE.POP cetyl ethers, POE.POP-2-decyltetradecyl ethers, POE.POP monobutyl ethers, POE-POP hydrated lanolin, POE.POP glycerin ethers; tetra-POE-tetra-POP ethylene diamine condensation products such as Tetronic; POE castor oil hydrogenated castor oil derivatives such as POE castor oil, POE hydrogenated castor oil, POE hydrogenated castor oil monoisostearate, POE hydrogenated castor oil triisostearate, POE hydrogenated castor oil monopyroglutamate monoisostearate diester, POE hydrogenated castor oil maleate; POE beeswax lanolin derivatives such as POE sorbitol beeswax; alkanolamides such as coconut oil fatty acid diethanolamide, lauric acid monoethanolamide, fatty acid isopropanolamide; POE propylene glycol fatty acid esters, POE alkylamines, POE fatty acid amides, sucrose fatty acid esters, POE nonylphenyl formaldehyde condensation products, alkylethoxydimethylamineoxide, trioleylphosphoric acid etc. may be mentioned.

As preservatives, methylparaben, ethylparabene, butylparaben, etc. may be mentioned.

As metal ion chelates, sodium edetate salts, EDTA, etc. may be mentioned.

As natural water-soluble polymers, plant base polymers such as gum arabic, tragacanth gum, galactan, guar gum, carob gum, karaya gum, carragheein, pectin, agar, quince seed (Marumero), algae colloid (seaweed extract), starch (rice, corn, potato, wheat), glycyrrhinic acid; microorganism base polymers such as xanthane gum, dextran, succinoglutan, pullulan; animal base polymers such as collagen, caseine, albumin, gelatin; etc. may be mentioned.

As semisynthesized water-soluble polymers, starch base polymers such as carboxymethyl starch, methylhydroxpropyl starch; cellulose base polymers such as methyl cellulose, nitro cellulose, ethyl cellulose, methylhydroxypropyl cellulose, hydroxyethyl cellulose, sodium cellulose sulfate, hydroxypropyl cellulose, sodium carboxymethyl cellulose (CMC), crystalline cellulose, cellulose powder; alginate base polymers such as sodium alginate, alginate propylene glycol esters; etc. may be mentioned.

As synthesized water-soluble polymers, vinyl base polymers such as a polyvinyl alcohol, polyvinylmethyl ether, polyvinylpyrrolidone, carboxyvinyl polymer (Carbopol), alkyl modified carboxyvinyl polymer; polyoxyethylene base polymers such as polyethylene glycol 2000, 4000, 6000; acryl base polymers such as polyoxyethylene polyoxypropylene copolymer base polymer, sodium polyacrylate, polyethylene acrylate, polyacryl amide, polyethylene imine, cationic polymer, etc. may be mentioned.

As inorganic water-soluble polymers, bentonite, AlMg silicate (bee gum), laponite, hectonite, inorganic silicic acid, etc. may be mentioned.

As the thickeners, carragheenin, karaya gum, tragacanth gum, carob gum, quince seed (Marumero), caseine, dextrin, gelatin, sodium pectinate, sodium alginate, methylcellulose, ethylcellulose, CMC, hydroxyethylcellulose, hydroxypropylcellulose, PVA, PVM, PVP, sodium polyacrylate, carboxyvinyl polymer, loqust bean gum, guar gum, tamarind gum, dialkyldimethyl ammonium sulfate cellulose, xanthane gum, aluminum magnesium silicate, bentonite, hectonite, etc. may be mentioned.

As powder components, inorganic powders such as talc, kaolin, mica, sericite, dolomite, phlogopite, synthetic mica, lepidolite, biotite, lithia mica, vermiculite, magnesium carbonate, calcium carbonate, aluminum silicate, barium silicate, calcium silicate, magnesium silicate, strontium silicate, metal salts of tungstenic acid, magnesium, silica, zeolite, barium sulfate, sintered calcium sulfate (sintered gypsum), calcium phosphate, fluorapatite, hydroxyapatite, ceramic powder, metal soap (zinc myristate, calcium palmitate, ammonium stearate), boronitride; organic powders such as polyamide resin powder (nylon powder), polyethylene powder, methyl polymethacrylate powder, polystyrene powder, styrene and acrylic acid copolymer resin powder, benzoguanamin resin powder, polytetrafluoroethylene powder, cellulose powder; inorganic white pigments such as titanium dioxide, zinc oxide; inorganic red pigments such as iron oxide (bengara), iron titanate; inorganic brown pigments such as γ-iron oxide; inorganic yellow pigments such as yellow iron oxide, yellow earth; inorganic black pigments such as black iron oxide, carbon black, lower titanium oxide; inorganic violet pigments such as mango violet, cobalt violet; inorganic green pigments such as chromium oxide, chromium hydroxide, cobalt titanate; inorganic blue pigments such as prussian blue, ultramarine; pearl pigments such as titanium oxide coated mica, titanium oxide coated bismuth oxichloride, titanium oxide coated talc, colored titanium oxide coated mica, bismuth oxichloride, fish scales; metal powder pigments such as aluminum powder, copper powder; lakes such as Lithol rubine B (Red No. 201), Lithol rubine BCA (Red No. 202), Lake red CBA (Red No. 204), Lithol red (Red No. 205), Deep maroon (Red No. 220), Helidone pink CN (Red No. 226), Permatone Red (Red No. 228), Permanent red F5R (Red No. 405), Permanent orange (Orange No. 203), Benzidine Orange (Orange No. 204), Benzidine yellow G (Yellow No. 205), Hanza Yellow (Yellow No. 401), Blue No. 404; zirconium, barium, or aluminum lakes and other lakes such as Erythrosine (Red No. 3), Phloxine B (Red No. 104), Acid red (Red No. 106), Fast acid magenta (Red No. 227), Eosine YS (Red No. 230), Violamine R (Red No. 401), Oil red XO (Red No. 505), Orange II (Orange No. 205), Tartrazine (Yellow No. 4), Sunset yellow FCF (Yellow No. 5), Uranine (Yellow No. 202), Quinoline yellow (Yellow No. 203), Fast green FCF (Green No. 3), Brilliant blue FCF (Blue No. 1); natural colors such as chlorophyl, β-carotin, coloring agents such as perfumes, water, alcohol, titanium yellow, carmine, Safflower Red; etc. may also be suitably formulated into the collagen production promoter composition of the present invention, if necessary.

EXAMPLES

The present invention will now be explained in further detail with reference to Examples, which by no means limits the present invention. Note that before these Examples, the methods of testing the effects and the results thereof will be explained.

(1) Test Example 1

(Evaluation of Action on Type I Collagen Producing Ability of Human Skin Fibroblast)

Human skin fibroblasts (hereinafter referred to as "cells") were used to evaluate the action of an extract of a shoot of a tree of the Fagaceae Fagus on the type I collagen biosynthesizing ability of cells. That is, 20,000 cells/well were inoculated in a 96-well plate (Corning: 25860) for cell culture. This was cultured in a RITC80-7 medium containing 10% fetal bovine serum (hereinafter referred to as "FBS") for 48 hours, then the medium was replaced with a RITC80-7 medium containing 0.5% FBS (hereinafter referred to as the "medium"). At this time, GATULINE (registered trademark) R (made by Gattfosse S. A.) was added to the medium. The concentrations of the GATULINE (registered trademark) R were made 0.01% and 0.1%. The medium was replaced with a medium containing GATULINE (registered trademark) R, then the cells were cultured for 48 hours. After the end of the culture, the cells of the culture supernatent were sampled for measurement of the amount of cells for measuring the type I collagen biosynthesis ability.

The type I collagen biosynthesis ability of the cells was evaluated by measuring the amount of Procollagen type IC-peptide (PIP) secreted into the culture supernatent. Specifically, this was measured using a "Procollagen type IC-peptide (PIP) measurement kit"(made by Takara Shuzo K.K.: MK001).

The amount of cells was estimated by the amount of DNA of the cells. The amount of DNA was measured using a Hoechst 33258 reagent according to the method of Cesar Lsbarca et al. (*Analytical Biochemisty*, 102, 344–352 (1980)).

The results are shown in FIG. 1. The amount of PIP increased according to the concentration of the extract from the shoot of the Fagus crenata. At 0.1%, a significant increase was observed. As explained above, the extract of the shoot of the Fagus crenata was observed to have the effect of promoting the type I collagen biosynthesis ability without affecting the proliferation of cells at extremely low concentrations of 0.01 to 0.1%.

(2) Test Example 2

(Monitor Test)

The following test of use was performed on creams obtained in Example 1 and Comparative Example 1 of the formulations shown in Table 1. The amounts formulated are shown in % by weight. The results are shown in Table 2.

TABLE 1

|      |                                      | Ex. 1   | Comp. Ex. 1 |
|------|--------------------------------------|---------|-------------|
| (1)  | Cetostearyl alcohol                  | 3.5     | 3.5         |
| (2)  | Squalane                             | 40.0    | 40.0        |
| (3)  | Beeswax                              | 3.0     | 3.0         |
| (4)  | Hydrogenated lanolin                 | 4.0     | 4.0         |
| (5)  | Ethylparaben                         | 0.3     | 0.3         |
| (6)  | Polyoxyethylene (20) sorbitan monopalmitate ester | 2.0 | 2.0 |
| (7)  | Monoglyceride stearate               | 2.0     | 2.0         |
| (8)  | GATULINE (registered trademark) RC   | 0.5     | —           |
| (9)  | Sodium N-stearoyl glutaminate        | 0.5     | 0.5         |
| (10) | Perfume                              | 0.03    | 0.03        |
| (11) | 1,3-butylene glycol                  | 5.0     | 5.0         |
| (12) | Polyethylene glycol 1500             | 5.0     | 5.0         |
| (13) | Purified water                       | Balance | Balance     |

Process of Production

The ingredients (1) to (10) shown in the above Table 1 were dissolved under heating (oil phase). On the other hand, (11) and (12) were dissolved in purified water (13) and held at 70° C. (aqueous phase). The oil phase was added to the aqueous phase while stirring. Next, the emulsion was processed by a homomixer to reduce the emulsion granules in size, then stirred, then rapidly cooled with stirring to obtain the desired cream.

Test Method

Eighty healthy adult women of ages 35 to 68 extracted at random were used as test subjects. They were asked to use the cosmetics on the skin of their faces daily for one month, then the effect of improvements in the tauttness and sagging of the skin and the effect of improvement of wrinkles and crow's feet were investigated.

Effect of Improvement of Tautness of Skin

The state of the skin was observed visually and evaluated based on the following evaluation criteria.

(Evaluation Criteria)

A: Extremely improved

B: Improved

C: No change

D: Became somewhat noticable

E: Became noticable

Effect of Improvement of Wrinkles and Crow's Feet

The state of the skin was observed visually and evaluated based on the following evaluation criteria.

(Evaluation Criteria)

A: Completely disappeared

B: Somewhat reduced

C: No change
D: Slightly increased
E: Increased

TABLE 2

|  | Effect on tautness and sagging (persons) | | | | | Effect on large wrinkles and crow's feet (persons) | | | | |
| --- | --- | --- | --- | --- | --- | --- | --- | --- | --- | --- |
|  | A | B | C | D | E | A | B | C | D | E |
| Ex. 1 | 50 | 19 | 11 | 0 | 0 | 36 | 34 | 10 | 0 | 0 |
| Comp. Ex. 1 | 2 | 12 | 63 | 2 | 1 | 1 | 9 | 67 | 3 | 0 |

As clear from the results shown in Table 2, in the case of use of the cosmetic obtained in Example 1, a remarkable improvement was observed in the tautness and sagging of the skin and there was an extremely high effect with respect to the wrinkles and crow's feet compared with the case of use of the cosmetic obtained in Comparative Example 1.

Example 2

Cream

| Formulation | wt % |
| --- | --- |
| Stearic acid | 2.0 |
| Stearyl alcohol | 7.0 |
| Hydrogenated lanolin | 2.0 |
| Squalane | 5.0 |
| 2-octyldodecyl alcohol | 6.0 |
| Polyoxyethylene (25 mol) cetyl alcohol ether | 3.0 |
| Glyceryl monostearate ester | 2.0 |
| Propylene glycol | 5.0 |
| Ethanol extract containing shoot of Fagus crenata | 5.0 |
| Tranexamic acid | 0.2 |
| Ethylparaben | 0.3 |
| Perfume | q.s. |
| Ion exchange water | Bal. |

Process of Production

The propylene glycol was added to the ion exchange water, then the mixture was heated and held at 70° C. (aqueous phase). The other ingredients were mixed and heated to melt, then the resultant mixture was held at 70° C. (oil phase). The oil phase was added to the aqueous phase and preliminarily emulsified and then emulsified uniformly by a homomixer, then the resultant mixture was rapidly cooled to 30° C. while stirring well.

Example 3

Cream

| Formulation | wt % |
| --- | --- |
| Solid paraffin | 5.0 |
| Beeswax | 10.0 |
| Vaseline | 15.0 |
| Liquid paraffin | 41.0 |
| Glyceryl monostearate ester | 2.0 |
| Polyoxyethylene (20 mol) sorbitan monolaurate ester | 2.0 |
| Soap powder | 0.1 |

-continued

| Formulation | wt % |
| --- | --- |
| Acetone extract of young shoot of Fagus crenata | 0.05 |
| Sodium bisulfite | 0.03 |
| Ethylparaben | 0.3 |
| Perfume | q.s. |
| Ion exchange water | Bal. |

Process of Production

The soap powder was added to the ion exchange water and heated and held at 70° C. (aqueous phase). The other ingredients were mixed and heated to melt, then held at 70° C. (oil phase). The oil phase was gradually added to the aqueous phase while stirring for the reaction. After the end of the reaction, the resultant mixture was uniformly emulsified by a homomixer. After the emulsification, the resultant mixture was cooled to 30° C. while stirring.

Example 4

Emulsion

| Formulation | wt % |
| --- | --- |
| Stearic acid | 2.5 |
| Cetyl alcohol | 1.5 |
| Vaseline | 5.0 |
| Liquid paraffin | 10.0 |
| Polyoxyethylene (10 mol) monooleate ester | 2.0 |
| Polyethylene glycol 1500 | 3.0 |
| Triethanolamine | 1.0 |
| Carboxyvinyl polymer (brandname: Carbopol 941, B.F. Goodrich Chemical Co.) | 0.05 |
| GATULINE (registered trademark) R | 0.01 |
| Sodium bisulfite | 0.01 |
| Ethylparaben | 0.3 |
| Perfume | q.s. |
| Ion exchange water | Bal. |

Process of Production

The carboxyvinyl polymer was dissolved in a small amount of ion exchange water (phase A). Polyethylene glycol 1500 and triethanolamine were added to the remaining ion exchange water, heated to melt, and held at 70° C. (aqueous phase). The rest of the ingredients were mixed and heated to melt, then held at 70° C. (oil phase). The oil phase was added to the aqueous phase and preliminarily emulsified, then the phase A was added and the mixture homogeneously emulsified by a homomixer. After the emulsification, the resultant mixture was cooled to 30° C. while stirring well.

Example 5

Emulsion

| Formulation | wt % |
| --- | --- |
| Microcrystalline wax | 1.0 |
| Beeswax | 2.0 |
| Lanolin | 20.0 |
| Liquid paraffin | 10.0 |
| Squalane | 5.0 |

-continued

| Formulation | wt % |
| --- | --- |
| Sorbitan sesquioleate ester | 4.0 |
| Polyoxyethylene (20 mol) sorbitan monooleate ester | 1.0 |
| Propylene glycol | 7.0 |
| Butanol extract of shoot of Fagus crenata | 10.0 |
| Tranexemic acid | 1.0 |
| Sodium bisulfite | 0.01 |
| Ethylparaben | 0.3 |
| Perfume | q.s. |
| Ion exchange water | Bal. |

Process of Production

The propylene glycol was added to the ion exchange water and then heated and held at 70° C. (aqueous phase). The rest of the ingredients were mixed and heated to melt then held at 70° C. (oil phase). The oil phase was gradually added to the aqueous phase while stirring and the two then homogeneously emulsified by a homomixer. After emulsification, the emulsion was cooled to 30° C. while stirring well.

Example 6

Jelly

| Formulation | wt % |
| --- | --- |
| 95% ethyl alcohol | 10.0 |
| Dipropylene glycol | 15.0 |
| Polyoxyethylene (50 mol) oleyl alcohol ether | 2.0 |
| Carboxyvinyl polymer (brandname: Carbopol 940, B.F. Goodrich Chemical Co.) | 0.05 |
| Caustic soda | 0.15 |
| L-arginine | 0.1 |
| Methanol aqueous solution extract of young shoot of Fagus crenata | 0.001 |
| Sodium bisulfite | 0.01 |
| Ethylparaben | 0.3 |
| Perfume | q.s. |
| Ion exchange water | Bal. |

Process of Production

The Carbopol 940 was homogeneously dissolved in the ion exchange water. On the other hand, the methanol aqueous solution extract of the young shoot of Fagus crenata and polyoxyethylene (50 mol) oleyl alcohol ether were dissolved in 95% ethanol and added to the aqueous phase. Next, the rest of the ingredients were added, then the resultant mixture was neutralized and thickened by the caustic soda and L-arginine.

Example 7

Jelly

| Formulation | wt % |
| --- | --- |
| (Phase A) | |
| Ethyl alcohol (95%) | 10.0 |
| Polyoxyethylene (20 mol) octyldodecanol | 1.0 |

-continued

| Formulation | wt % |
| --- | --- |
| Pantothenyl ethyl ether | 0.1 |
| 1,3-butylene glycol extract of young shoot of Fagus crenata | 1.5 |
| Ethylparaben | 0.15 |
| (Phase B) | |
| Potassium hydroxide | 0.1 |
| (Phase C) | |
| Glycerin | 5.0 |
| Dipropylene glycol | 10.0 |
| Sodium bisulfite | 0.03 |
| Carboxyvinyl polymer (brandname: Carbopol 940, B.F. Goodrich Chemical Co.) | 0.2 |
| Purified water | Bal. |

Process of Production

Phase A and Phase C were each homogeneously dissolved, the Phase A was added to Phase C to solubilize it. Next, Phase B was added, then the resultant mixture filled into containers.

Example 8

Pack

| Formulation | wt % |
| --- | --- |
| (Phase A) | |
| Dipropylene glycol | 5.0 |
| Polyoxyethylene (60 mol) hydrogenated castor oil | 5.0 |
| (Phase B) | |
| Acetone extract of shoot of Fagus crenata | 0.01 |
| Olive oil | 5.0 |
| Tocopherol acetate | 0.2 |
| Ethylparaben | 0.2 |
| Perfume | 0.2 |
| (Phase C) | |
| Sodium bisulfite | 0.03 |
| Polyvinyl alcohol (saponification value 90, polymerization degree 2,000) | 13.0 |
| Ethanol | 7.0 |
| Purified water | Bal. |

Process of Production

Phase A, Phase B, and Phase C were each homogeneously dissolved, then Phase B were added to Phase A to solubilize it. Next, this was added to Phase C, then the resultant mixture filled in containers.

Example 9

Sunburn Prevention Cosmetic

| Formulation | wt % |
| --- | --- |
| Stearic acid | 1.5 |
| Cetyl alcohol | 3.0 |
| Beeswax | 2.0 |
| Polyoxyethylene (10 mol) monooleate | 1.0 |

-continued

| Formulation | wt % |
| --- | --- |
| ester | |
| Glyceryl monostearate ester | 1.0 |
| Dimethyl polysiloxane | 10.0 |
| Decamethyl cyclopentasiloxane | 20.0 |
| 2-hydroxy-4-methoxybenzophenon | 3.0 |
| Octyl-p-methoxycinnamate | 2.0 |
| GATULINE (registered trademark) R | 0.1 |
| Perfume | q.s. |
| Ion exchange water | Bal. |

Example 10

Cosmetic Foundation

A W/O emulsion type cosmetic foundation of the following composition was prepared:

| Formulation | wt % |
| --- | --- |
| Organic modified montmorillonite | 0.5 |
| Cetyl isooctanate | 2.0 |
| Octamethyl cyclotetrasiloxane | 2.0 |
| Decamethyl cyclopentasiloxane | 5.0 |
| Dimethyl polysiloxane (6 cs) | 5.0 |
| Liquid paraffin | 3.0 |
| Dioctadecyldimethyl ammonium chloride | 0.2 |
| Polyoxyalkylene modified organopolysiloxane | 5.0 |
| 4-t-butyl-4'-methoxydibenzoylmethane | 0.3 |
| Glyceryl mono-2-ethylhexanoyldipara-methoxycinnamate | 1.0 |
| Microgranular titanium oxide | 5.0 |
| Oleyl alcohol | 0.5 |
| Stearic acid | 0.5 |
| Sorbitan diisostearate | 4.0 |
| Antioxidant | q.s. |
| Perfume | q.s. |
| Talc | 1.5 |
| Nylon powder | 1.0 |
| Ion exchange water | Bal. |
| Sodium citrate | 0.5 |
| 1,3-butylene glycol | 5.0 |
| GATULINE (registered trademark) RC | 0.01 |

Example 11

Powdery Foundation

| Formulation | wt % |
| --- | --- |
| Microgranular titanium oxide | 7.0 |
| Talc | 40.0 |
| Mica | Bal. |
| Nylon powder | 10.0 |
| Red iron oxide | 1.0 |
| Yellow iron oxide | 2.0 |
| Black iron oxide | 0.2 |
| Dimethyl polysiloxane | 1.0 |
| 2-ethylhexyl palmitate | 9.0 |
| Sorbitan sesquioleate | 1.0 |
| N,N-dimethyl PABA octyl ester | 0.3 |
| Ethyl acetate ester extract of shoot of Fagus crenata | 5.0 |
| Preservative | q.s. |
| Antioxidant | q.s. |
| Perfume | q.s. |

Example 12

Oily Foundation

| Formulation | wt % |
| --- | --- |
| Microgranular titanium oxide | 10.0 |
| Mica | 22.4 |
| Kaolin | 10.0 |
| Nylon powder | 5.0 |
| Red iron oxide | 0.5 |
| Yellow iron oxide | 2.0 |
| Black iron oxide | 0.1 |
| Liquid paraffin | Bal. |
| Dimethylpolysiloxane | 10.0 |
| Sorbitan sesquioleate | 2.0 |
| Octylmethoxycinnamate | 5.0 |
| Extract of shoot belonging to Fagus crenata | 0.005 |
| Perfume | q.s. |
| Microcrystalline wax | 6.0 |
| Carnauba wax | 3.0 |

INDUSTRIAL APPLICABILITY

As explained above, the collagen production promoter composition of the present invention exhibits a superior effect of prevention of aging by promoting the production of collagen, which is one of the components of the extracellular matrix, and the activation of the excellular matrix and normalization of the skin tissue based on the promotion production of collagen.

What is claimed is:

1. A method for promoting collagen production in a fibroblast of a subject comprising topically administering to said subject a collagen production promoter composition in an amount effective to promote collagen production in a fibroblast, wherein said composition comprises, as active components, (i) 0.0001 to 30.0% by weight, based upon the total weight of the composition, of an extract obtained by extracting a shoot of *Fagus crenata* with at least one solvent, wherein the solvent is selected from the group consisting of water, ethanol, methanol, propanol, butanol, 1,3-butylene glycol and any mixtures thereof, and (ii) vitamin C in an amount effective for synergistic promotion of collagen production.

2. A method as claimed in claim in 1 wherein the extract from a shoot of a *Fagus crenata* is contained in a range of 0.0001 to 10.0% by weight based upon the total weight of the composition.

* * * * *